United States Patent
Srinivasan

(10) Patent No.: US 11,202,618 B2
(45) Date of Patent: Dec. 21, 2021

(54) SNR IMPROVEMENT AND OPERATOR-INDEPENDENCE USING TIME-VARYING FRAME-SELECTION FOR STRAIN ESTIMATION

(71) Applicant: EDAN INSTRUMENTS, INC., Shenzhen (CN)

(72) Inventor: Seshadri Srinivasan, Sunnyvale, CA (US)

(73) Assignee: EDAN INSTRUMENTS, INC., Shenzhen (CN)

( * ) Notice: Subject to any disclaimer, the term of this patent is extended or adjusted under 35 U.S.C. 154(b) by 245 days.

(21) Appl. No.: 15/271,019

(22) Filed: Sep. 20, 2016

(65) Prior Publication Data
US 2017/0079619 A1     Mar. 23, 2017

Related U.S. Application Data

(60) Provisional application No. 62/221,513, filed on Sep. 21, 2015.

(51) Int. Cl.
*A61B 8/08*     (2006.01)
*A61B 8/00*     (2006.01)

(52) U.S. Cl.
CPC ............ *A61B 8/485* (2013.01); *A61B 8/4427* (2013.01); *A61B 8/5269* (2013.01); *A61B 8/5215* (2013.01)

(58) Field of Classification Search
CPC ..... A61B 8/485; A61B 8/4427; A61B 8/5269; A61B 8/5215
See application file for complete search history.

(56) References Cited

U.S. PATENT DOCUMENTS

| | | | | |
|---|---|---|---|---|
| 5,474,070 A | * | 12/1995 | Ophir | A61B 5/0048 600/437 |
| 6,508,768 B1 | * | 1/2003 | Hall | A61B 8/08 600/443 |
| 6,558,324 B1 | * | 5/2003 | Von Behren | A61B 8/08 600/437 |
| 7,632,230 B2 | * | 12/2009 | Varghese | A61B 8/08 600/438 |
| 9,125,618 B2 | * | 9/2015 | Park | A61B 5/0048 |
| 2006/0285731 A1 | * | 12/2006 | Jiang | G01S 7/52042 382/128 |
| 2007/0093716 A1 | * | 4/2007 | Radulescu | A61B 8/08 600/437 |
| 2008/0214934 A1 | * | 9/2008 | Lee | A61B 8/481 600/437 |

(Continued)

OTHER PUBLICATIONS

Souchon et al. (2002). Ultrasonic elastography using sector scan imaging and a radial compression. Ultrasonics. 40:867-871 (Year: 2002).*

*Primary Examiner* — Angela M Hoffa
*Assistant Examiner* — Younhee Choi

(57) ABSTRACT

An ultrasound processing system includes an ultrasound interface and processing electronics. The ultrasound interface receives imaging information. The processing electronics are coupled to the ultrasound interface and are configured to utilize the ultrasound imaging information to use time-varying frame selection to estimate strain so that the processing electronics perform the time-varying frame selection by comparing a single frame to a plurality of previous frames and selecting a single comparison set for each frame for strain estimation.

21 Claims, 11 Drawing Sheets

(56) References Cited

U.S. PATENT DOCUMENTS

| | | | |
|---|---|---|---|
| 2009/0221916 A1* | 9/2009 | Konofagou | A61B 5/4514 600/443 |
| 2010/0256494 A1* | 10/2010 | Azuma | A61B 8/08 600/443 |
| 2011/0237945 A1* | 9/2011 | Foroughi | A61B 8/4245 600/438 |
| 2016/0007965 A1* | 1/2016 | Murphy | G01S 7/52084 345/173 |
| 2016/0331345 A1* | 11/2016 | Kong | A61B 8/485 |

* cited by examiner

| Current Frame | Frames to compare | Mean Strain in (1st half of image) | Selected frames for final strain estimation |
|---|---|---|---|
| f4 | f4*f3 | 2% | f4*f2 |
|  | f4*f2 | 1% |  |
|  | f4*f1 | 3% |  |
|  | f4*f0 | 4% |  |
| f5 | f5*f4 | 2% | f5*f1 |
|  | f5*f3 | 4% |  |
|  | f5*f2 | 3% |  |
|  | f5*f1 | 1% |  |
| ... | ... | ... | ... |

FIG. 5A

| Current Frame | Frames to compare | Mean Strain in (1st half of image / 2nd half of image) | Selected frames for final strain estimation (first half / Second half) |
|---|---|---|---|
| f4 | f4*f3 | 2% / 0.4% | f4*f2 / (f4*f0)/5 |
|  | f4*f2 | 1% / 0.2% |  |
|  | f4*f1 | 3% / 0.6% |  |
|  | f4*f0 | 4% / 0.8% |  |
| f5 | f5*f4 | 2% / 0.4% | f5*f1 / (f5*f3)/5 |
|  | f5*f3 | 4% / 0.8% |  |
|  | f5*f2 | 3% / 0.6% |  |
|  | f5*f1 | 1% / 0.2% |  |

FIG. 5B

SNR IMPROVEMENT AND OPERATOR-INDEPENDENCE USING TIME-VARYING FRAME-SELECTION FOR STRAIN ESTIMATION

CROSS-REFERENCE TO RELATED APPLICATIONS

This application claims the benefit of and priority to U.S. Provisional Patent Application No. 62/221,513, titled "SNR IMPROVEMENT AND OPERATOR-INDEPENDENCE USING TIME-VARYING FRAME SELECTION FOR STRAIN ESTIMATION," filed Sep. 21, 2015, the entire disclosure of which is incorporated herein by reference in its entirety.

BACKGROUND

The present disclosure relates generally to ultrasound systems that include processing electronics. More specifically, the present disclosure relates to a strain estimation processor in an ultrasound system that performs elastography to improve the signal to noise ratio of an image.

Elastography is an imaging modality commonly available in commercial ultrasound systems that allows for the mapping of elastic properties of soft tissue. To achieve an elastography image, a distortion is induced and the resulting deformation is viewed. The distortion can be caused by pushing or vibrating the surface of the body with an ultrasound probe, or another device. The distortion can then be used to determine the stiffness of the tissues. The distortion can also be caused by ultrasound waves to create a 'push' or a high or low frequency mechanical wave inside the tissue. For any given applied force, softer tissue deforms more than stiffer tissue. In addition, mechanical waves travel faster through stiffer tissue than softer tissue. This information can be used to determine the stiffness of a given tissue. One of the main problems in elastography is the time-variation of strain image that impacts its utility. As pressure is changed, the image is changing as the deformation changes. However, imaging parameters are not changed with respect to the changing image over time. Conventional persistence address the time-variation issue, at the expense of signal-to-noise ratio (SNR). Conventional persistence is a technique where multiple frames are combined or averaged into a single image. While this address the time-variation issue, it does not improve SNR because the variations of displacement are not taken into account when averaging, creating noise.

Conventional elastography ultrasound systems techniques fail to address time-variation while maintaining SNR. It would be desirable to have processing electronics to normalize strain over time to ensure adequate quality of elastography without reducing SNR. These techniques may include estimating strain using multiple frames and frames that produce the best SNR. The benefits of these processing electronics include improving SNR as well as reducing the operator-dependence of compression.

SUMMARY

One implementation of the present disclosure relates to an ultrasound processing system. The ultrasound system includes an ultrasound interface that receives ultrasound imaging information. The ultrasound system further includes processing electronics coupled to the ultrasound interface and configured to utilize the ultrasound imaging information to use time-varying frame selection to estimate strain and/or displacement and the processing electronics perform the time-varying frame selection by comparing a single frame to a plurality of previous frames and selecting a single comparison set for each frame for strain and/or displacement estimation.

In some embodiments, the processing electronics use multi-frame displacement estimation for comparing frames.

In some embodiments, the processing electronics select frame comparison sets with adequate mean strain.

In some embodiments, the processing electronics select frame comparison sets with the best signal to noise ratio.

In some embodiments, the processing electronics may select different frame comparison sets for different depths.

In some embodiments, the strain and/or displacement is estimated by normalizing the strain and/or displacement estimation.

In some embodiments, the processing electronics only display strain and/or displacement images that have a strain and/or displacement meeting given criteria.

In some embodiments, the processing electronics use a desired strain and/or displacement for the given criteria.

In some embodiments, the desired strain is input by the user.

In some embodiments, the processing electronics select the frame comparison sets to use based on the desired strain and/or displacement.

In some embodiments, the processing electronics select the frame comparison set to use based on a weighted system.

In some embodiments, the weighted system includes strain and/or displacement average and desired strain and/or displacement.

In some embodiments, the processing electronics predict a periodicity of motion.

In some embodiments, the periodicity of motion is determined using the history of mean displacement over time.

In some embodiments, the processing electronics feedback the selected frame comparisons sets.

In some embodiments, the feedback of the selected frame comparisons sets is used in previous cycles for strain and/or displacement estimation Another implementation of the present disclosure relates to an ultrasound machine. The ultrasound machine includes an ultrasound engine configured to receive ultrasound returns representative of an ultrasound scene for display and an ultrasound processor configured to normalize strain for displacement and/or strain estimation. The ultrasound processor causes a display output to be generated after processing the displacement and/or strain estimation using frame comparison sets.

Another implementation of the present disclosure relates to a method of signal to noise ratio improvement in elastography using time-varying frame selection strain estimation, which includes: receiving imaging and displacement and/or strain data; comparing each frame to previous frames; selecting a frame comparison set for each frame; estimating a final displacement and/or strain; processing imaging data; and displaying an image.

In some embodiments, after a defined period, the determined comparison sets are used to estimate the final displacement and/or strain through feedback.

In some embodiments, the image is divided into depth sections.

In some embodiments, different frame comparison sets can be selected for the same frame based on depth.

In some embodiments, the estimated final strain is estimated by normalizing the displacement and/or strain estimation.

In some embodiments, the frame comparison sets are selected based on mean displacement and/or strain.

In some embodiments, the frame comparison sets are selected based on SNR.

In some embodiments, the frame comparison sets are selected based on a combination of factors.

BRIEF DESCRIPTION OF THE DRAWINGS

FIG. 5A is a table of the frame comparisons and frame comparison sets of FIG. 3A, according to an exemplary embodiment.

FIG. 5B is a table of the frame comparisons and frame comparison sets of depth variation of FIG. 3B, according to an exemplary embodiment.

DETAILED DESCRIPTION

Referring generally to the FIGURES, systems and methods for strain estimation are shown, according to various exemplary embodiments. The systems and methods described herein may be used to improve SNR in elastographic imaging. For example, the SNR may be improved by using time-varying frame selection.

The present disclosure generally relates to systems and methods for adaptively improving SNR in an ultrasound system using time-varying frame selection processing. A time-varying frame selection processor is used as an example in the various figures to help illustrate the present disclosure. However, it should be recognized that the present disclosure can be applied to a wide variety of processing electronics and other electronic devices that process imaging data.

In one embodiment of the present disclosure, an elastography ultrasound system includes a time-varying frame selection processor configured to compare each frame to previous frames and compare these comparisons. The processing electronics select a comparison set for each frame to estimate the final strain for image display. The processing electronics may be configured to select frame comparison sets based on SNR. The processing electronics may be configured to select frame comparison sets based on adequate mean strain.

Figure 1A:
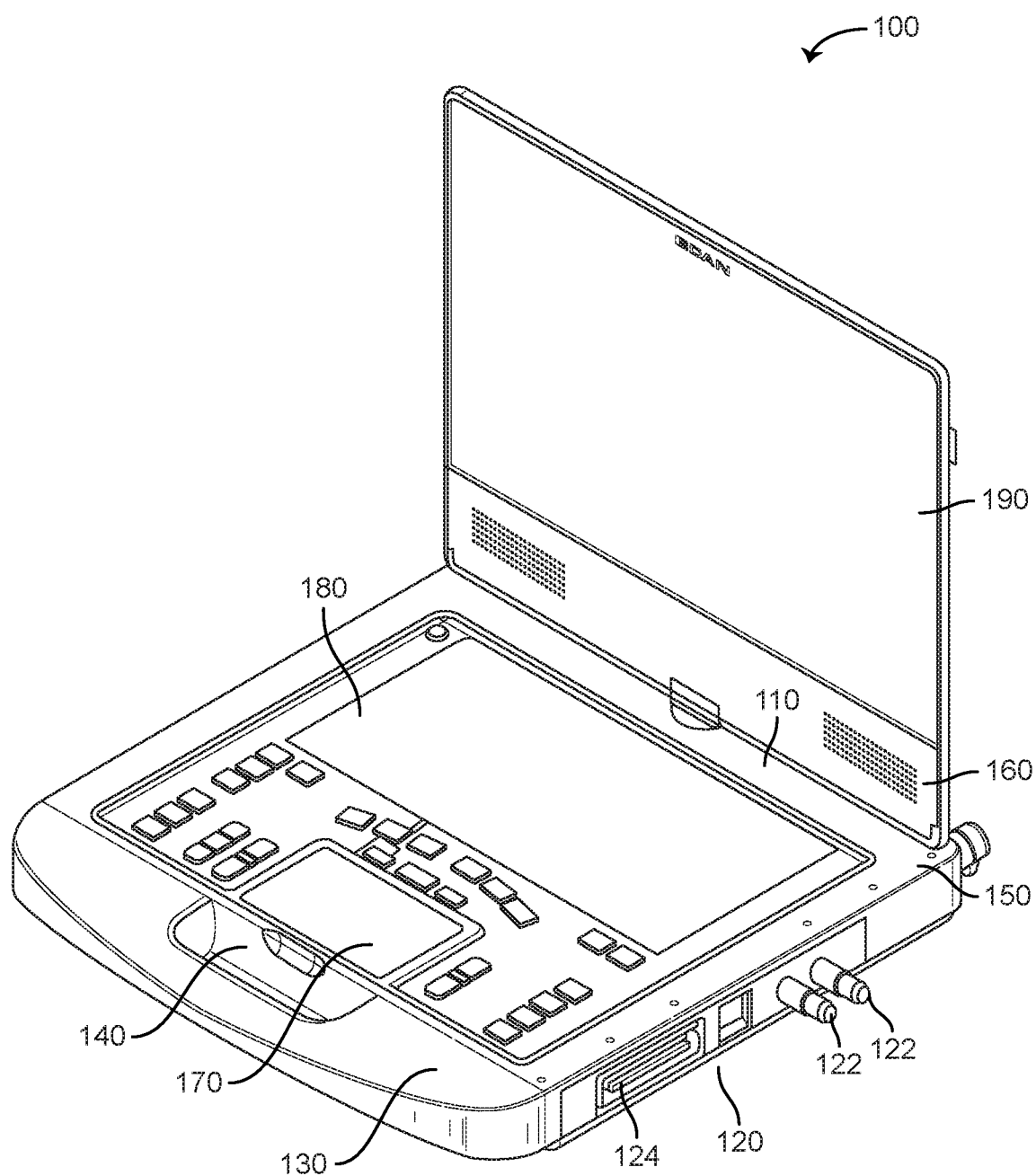
FIG. 1A is a drawing of a portable ultrasound system, according to an exemplary embodiment.

Referring now to FIG. 1A, one embodiment of portable ultrasound system 100 is illustrated. Portable ultrasound system 100 may include display support system 110 for increasing the durability of the display system. Portable ultrasound system 100 may further include locking lever system 120 for securing ultrasound probes and/or transducers. Some embodiments of portable ultrasound system 100 include ergonomic handle system 130 for increasing portability and usability. Further embodiments include status indicator system 140 which displays, to a user, information relevant to portable ultrasound system 100. Portable ultrasound system 100 may further include features such as an easy to operate and customizable user interface, adjustable feet, a backup battery, modular construction, cooling systems, etc.

Still referring to FIG. 1A, main housing 150 houses components of portable ultrasound system 100. In some embodiments, the components housed within main housing 150 include locking lever system 120, ergonomic handle system 130, and status indicator system 140. Main housing 150 may also be configured to support electronics modules which may be replaced and/or upgraded due to the modular construction of portable ultrasound system 100. In some embodiments, portable ultrasound system 100 includes display housing 160. Display housing 160 may include display support system 110. In some embodiments, portable ultrasound system 100 includes touchpad 170 for receiving user inputs and displaying information, touchscreen 180 for receiving user inputs and displaying information, and main screen 190 for displaying information.

Figure 1B:
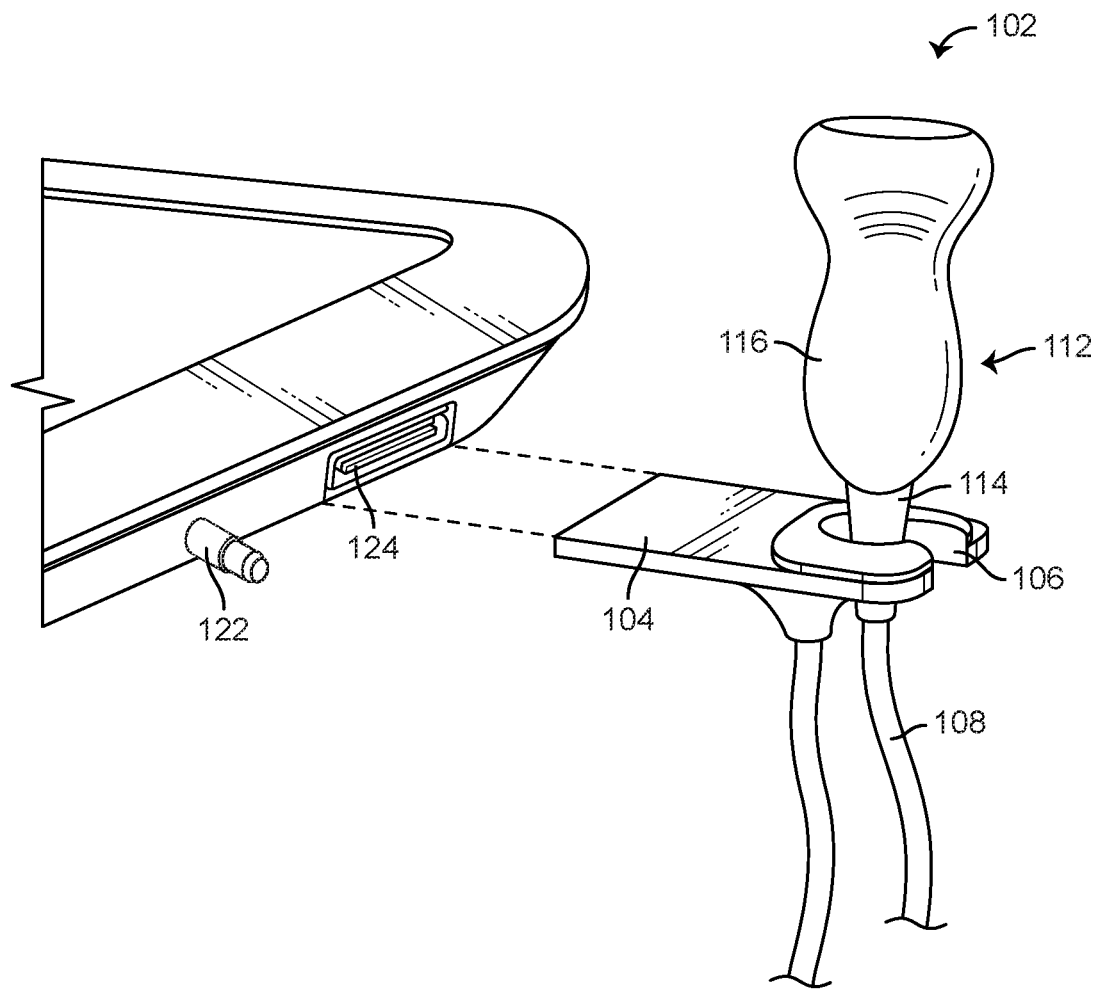
FIG. 1B is a drawing of an ultrasound transducer assembly for coupling to the portable ultrasound system of FIG. 1A, according to an exemplary embodiment.

Referring now to FIG. 1B, ultrasound transducer assembly 102 is shown. According to an exemplary embodiment, ultrasound transducer assembly 102 includes a connection assembly to a pin (122) or socket (124) type ultrasound interface, shown as ultrasound interface connector 104, coupled to a cable 108. Cable 108 may be coupled to a transducer probe 112. While FIG. 1B shows only one transducer assembly 102, more transducer assemblies may be coupled to the ultrasound system 100 based on the quantity of pin (122) or socket (124) type ultrasound interfaces.

Ultrasound interface connector 104 is movable between a removed position with respect to the pin (122) or socket (124) type ultrasound interface, in which ultrasound interface connector 104 is not received by the pin (122) or socket (124) type ultrasound interface, a partially connected position, in which ultrasound interface connector 104 is partially received by the pin (122) or socket (124) type ultrasound interface, and a fully engaged position, in which ultrasound interface connector 104 is fully received by the pin (122) or socket (124) type ultrasound interface in a manner that electrically couples transducer probe 112 to ultrasound system 100. In an exemplary embodiment, the pin (122) or socket (124) type ultrasound interface may include a sensor or switch that detects the presence of the ultrasound interface connector 104.

In various exemplary embodiments contained herein, the ultrasound interface connector 104 may house passive or active electronic circuits for affecting the performance of the connected transducers. For example, in some embodiments the transducer assembly 102 may include filtering circuitry, processing circuitry, amplifiers, transformers, capacitors, batteries, failsafe circuits, or other electronics which may customize or facilitate the performance of the transducer and/or the overall ultrasound machine. In an exemplary embodiment, ultrasound interface connector 104 may include a bracket 106, where the transducer probe 112 may be stored when not in use.

Transducer probe 112 transmits and receives ultrasound signals that interact with the patient during the diagnostic ultrasound examination. The transducer probe 112 includes a first end 114 and a second end 116. The first end 114 of the transducer probe 112 may be coupled to cable 108. The first end 114 of the transducer probe 112 may vary in shape to properly facilitate the cable 108 and the second end 116. The second end 116 of the transducer probe 174 may vary in shape and size to facilitate the conduction of different types of ultrasound examinations. These first end 114 and second end 116 of transducer probe 112 variations may allow for better examination methods (e.g., contact, position, location, etc.).

A user (e.g., a sonographer, an ultrasound technologist, etc.) may remove a transducer probe 112 from a bracket 106 located on ultrasound interface connector 104, position transducer probe 112, and interact with main screen 190 to conduct the diagnostic ultrasound examination. Conducting the diagnostic ultrasound examination may include pressing transducer probe 112 against the patient's body or placing a variation of transducer probe 112 into the patient and causing the tissue to deform. The ultrasound image acquired may be viewed on main screen 190.

Figure 2:
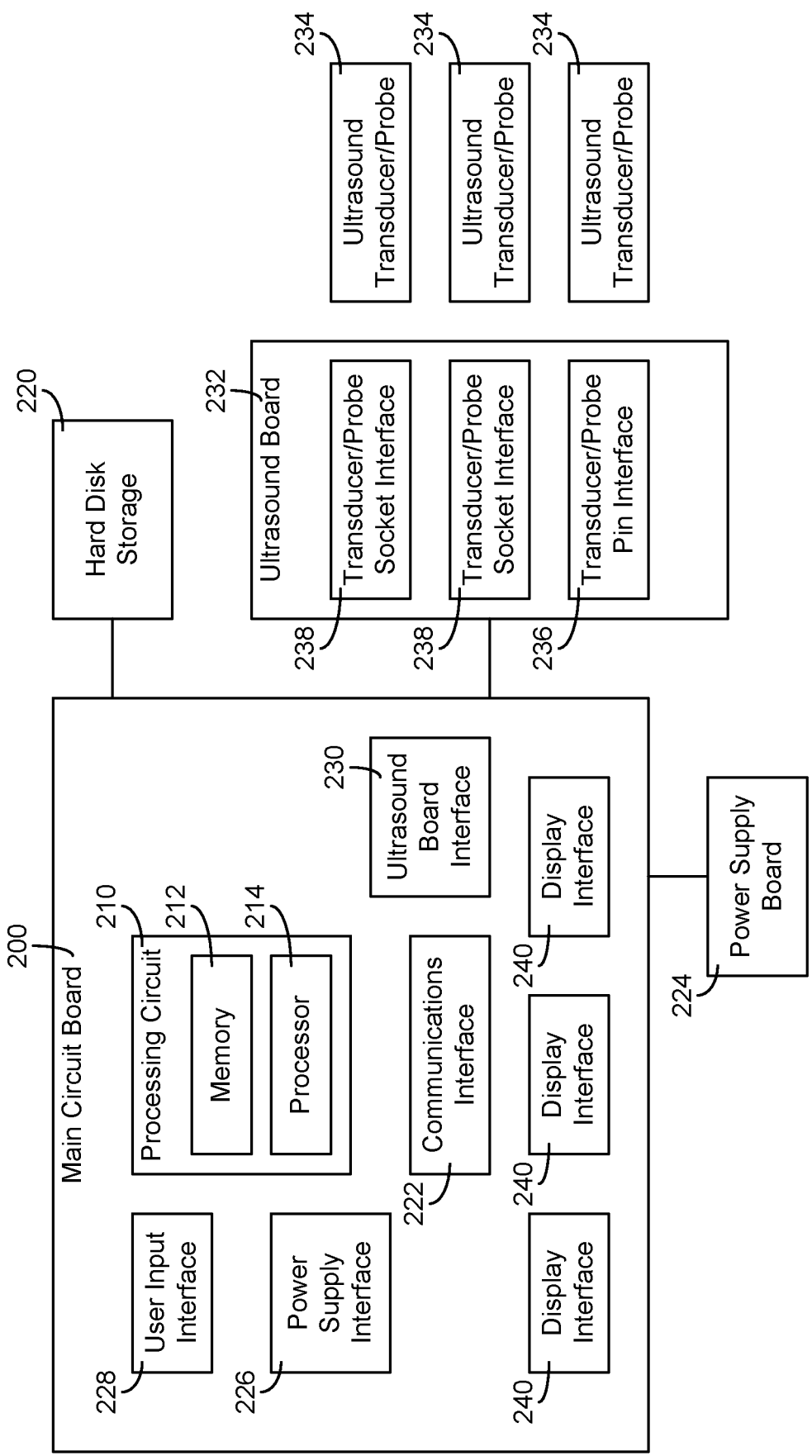
FIG. 2 is a block diagram illustrating components of one embodiment of a portable ultrasound system.

Referring to FIG. 2, a block diagram shows internal components of one embodiment of portable ultrasound system 100. Portable ultrasound system 100 includes main circuit board 200. Main circuit board 200 carries out computing tasks to support the functions of portable ultrasound system 100 and provides connection and communication between various components of portable ultrasound system 100. In some embodiments, main circuit board 200 is configured so as to be a replaceable and/or upgradable module.

To perform computational, control, and/or communication tasks, main circuit board 200 includes processing circuit 210. Processing circuit 210 is configured to perform general processing and to perform processing and computational tasks associated with specific functions of portable ultrasound system 100. For example, processing circuit 210 may perform calculations and/or operations related to producing an image from signals and or data provided by ultrasound equipment, running an operating system for portable ultrasound system 100, receiving user inputs, etc. Processing circuit 210 may include memory 212 and processor 214 for use in processing tasks. For example, processing circuit 210 may perform calculations and/or operations.

Processor 214 may be, or may include, one or more microprocessors, application specific integrated circuits (ASICs), circuits containing one or more processing components, a group of distributed processing components, circuitry for supporting a microprocessor, or other hardware configured for processing. Processor 214 is configured to execute computer code. The computer code may be stored in memory 212 to complete and facilitate the activities described herein with respect to portable ultrasound system 100. In other embodiments, the computer code may be retrieved and provided to processor 214 from hard disk storage 220 or communications interface 222 (e.g., the computer code may be provided from a source external to main circuit board 200).

Memory 212 may be any volatile or non-volatile computer-readable storage medium capable of storing data or computer code relating to the activities described herein. For example, memory 212 may include modules which are computer code modules (e.g., executable code, object code, source code, script code, machine code, etc.) configured for execution by processor 214. Memory 212 may include computer executable code related to functions including ultrasound imaging, battery management, handling user inputs, displaying data, transmitting and receiving data using a wireless communication device, etc. In some embodiments, processing circuit 210 may represent a collection of multiple processing devices (e.g., multiple processors, etc.). In such cases, processor 214 represents the collective processors of the devices and memory 212 represents the collective storage devices of the devices. When executed by processor 214, processing circuit 210 is configured to complete the activities described herein as associated with portable ultrasound system 100.

Hard disk storage 220 may be a part of memory 212 and/or used for non-volatile long term storage in portable ultrasound system 100. Hard disk storage 220 may store local files, temporary files, ultrasound images, patient data, an operating system, executable code, and any other data for supporting the activities of portable ultrasound device 100 described herein. In some embodiments, hard disk storage 220 is embedded on main circuit board 200. In other embodiments, hard disk storage 220 is located remote from main circuit board 200 and coupled thereto to allow for the transfer of data, electrical power, and/or control signals. Hard disk storage 220 may be an optical drive, magnetic drive, a solid state hard drive, flash memory, etc.

In some embodiments, main circuit board 200 includes communications interface 222. Communications interface 222 may include connections which enable communication between components of main circuit board 200 and communications hardware. For example, communications interface 222 may provide a connection between main circuit board 200 and a network device (e.g., a network card, a wireless transmitter/receiver, etc.). In further embodiments, communications interface 222 may include additional circuitry to support the functionality of attached communications hardware or to facilitate the transfer of data between communications hardware and main circuit board 200. In other embodiments, communications interface 222 may be a system on a chip (SOC) or other integrated system which allows for transmission of data and reception of data. In such a case, communications interface 222 may be coupled directly to main circuit board 200 as either a removable package or embedded package.

Some embodiments of portable ultrasound system 100 include power supply board 224. Power supply board 224 includes components and circuitry for delivering power to components and devices within and/or attached to portable ultrasound system 100. In some embodiments, power supply board 224 includes components for alternating current and direct current conversion, for transforming voltage, for delivering a steady power supply, etc. These components may include transformers, capacitors, modulators, etc. to perform the above functions. In further embodiments, power supply board 224 includes circuitry for determining the available power of a battery power source. In other embodiments, power supply board 224 may receive information regarding the available power of a battery power source from circuitry located remote from power supply board 224. For example, this circuitry may be included within a battery. In some embodiments, power supply board 224 includes circuitry for switching between power sources. For example, power supply board 224 may draw power from a backup battery while a main battery is switched. In further embodiments, power supply board 224 includes circuitry to operate as an uninterruptable power supply in conjunction with a backup battery. Power supply board 224 also includes a connection to main circuit board 200. This connection may allow power supply board 224 to send and receive information from main circuit board 200. For example, power supply board 224 may send information to main circuit board 200 allowing for the determination of remaining battery power. The connection to main circuit board 200 may also allow main circuit board 200 to send commands to power supply board 224. For example, main circuit board 200 may send a command to power supply board 224 to switch from one source of power to another (e.g., to switch to a backup battery while a main battery is switched). In some embodiments, power supply board 224 is configured to be a module. In such cases, power supply board 224 may be configured so as to be a replaceable and/or upgradable module. In some embodiments, power supply board 224 is or includes a power supply unit. The power supply unit may convert AC power to DC power for use in portable ultrasound system 100. The power supply may perform additional functions such as short circuit protection, overload protection, undervoltage protection, etc. The power supply may conform to ATX specification. In other embodiments, one or more of the above described functions may be carried out by main circuit board 200.

Main circuit board 200 may also include power supply interface 226 which facilitates the above described communication between power supply board 224 and main circuit board 200. Power supply interface 226 may include connections which enable communication between components of main circuit board 200 and power supply board 224. In further embodiments, power supply interface 226 includes additional circuitry to support the functionality of power supply board 224. For example, power supply interface 226 may include circuitry to facilitate the calculation of remaining battery power, manage switching between available power sources, etc. In other embodiments, the above described functions of power supply board 224 may be carried out by power supply interface 226. For example, power supply interface 226 may be a SOC or other integrated system. In such a case, power supply interface 226 may be coupled directly to main circuit board 200 as either a removable package or embedded package.

With continued reference to FIG. 2, some embodiments of main circuit board 200 include user input interface 228. User input interface 228 may include connections which enable communication between components of main circuit board 200 and user input device hardware. For example, user input interface 228 may provide a connection between main circuit board 200 and a capacitive touchscreen, resistive touchscreen, mouse, keyboard, buttons, and/or a controller for the proceeding. In one embodiment, user input interface 228 couples controllers for touchpad 170, touchscreen 180, and main screen 190 to main circuit board 200. In other embodiments, user input interface 228 includes controller circuitry for touchpad 170, touchscreen 180, and main screen 190. In some embodiments, main circuit board 200 includes a plurality of user input interfaces 228. For example, each user input interface 228 may be associated with a single input device (e.g., touchpad 170, touchscreen 180, a keyboard, buttons, etc.).

In further embodiments, user input interface 228 may include additional circuitry to support the functionality of attached user input hardware or to facilitate the transfer of data between user input hardware and main circuit board 200. For example, user input interface 228 may include controller circuitry so as to function as a touchscreen controller. User input interface 228 may also include circuitry for controlling haptic feedback devices associated with user input hardware. In other embodiments, user input interface 228 may be a SOC or other integrated system which allows for receiving user inputs or otherwise controlling user input hardware. In such a case, user input interface 228 may be coupled directly to main circuit board 200 as either a removable package or embedded package.

Main circuit board 200 may also include ultrasound board interface 230 which facilitates communication between ultrasound board 232 and main circuit board 200. Ultrasound board interface 230 may include connections which enable communication between components of main circuit board 200 and ultrasound board 232. In further embodiments, ultrasound board interface 230 includes additional circuitry to support the functionality of ultrasound board 232. For example, ultrasound board interface 230 may include circuitry to facilitate the calculation of parameters used in generating an image from ultrasound data provided by ultrasound board 232. In some embodiments, ultrasound board interface 230 is a SOC or other integrated system. In such a case, ultrasound board interface 230 may be coupled directly to main circuit board 200 as either a removable package or embedded package.

In other embodiments, ultrasound board interface 230 includes connections which facilitate use of a modular ultrasound board 232. Ultrasound board 232 may be a module (e.g., ultrasound module) capable of performing functions related to ultrasound imaging (e.g., multiplexing sensor signals from an ultrasound probe/transducer, controlling the frequency of ultrasonic waves produced by an ultrasound probe/transducer, etc.). The connections of ultrasound board interface 230 may facilitate replacement of ultrasound board 232 (e.g., to replace ultrasound board 232 with an upgraded board or a board for a different application). For example, ultrasound board interface 230 may include connections which assist in accurately aligning ultrasound board 232 and/or reducing the likelihood of damage to ultrasound board 232 during removal and/or attachment (e.g., by reducing the force required to connect and/or remove the board, by assisting, with a mechanical advantage, the connection and/or removal of the board, etc.).

In embodiments of portable ultrasound system 100 including ultrasound board 232, ultrasound board 232 includes components and circuitry for supporting ultrasound imaging functions of portable ultrasound system 100. In some embodiments, ultrasound board 232 includes integrated circuits, processors, and memory. Ultrasound board 232 may also include one or more transducer/probe socket interfaces 238. Transducer/probe socket interface 238 enables ultrasound transducer/probe 234 (e.g., a probe with a socket type connector) to interface with ultrasound board 232. For example, transducer/probe socket interface 238 may include circuitry and/or hardware connecting ultrasound transducer/probe 234 to ultrasound board 232 for the transfer of electrical power and/or data. Transducer/probe socket interface 238 may include hardware which locks ultrasound transducer/probe 234 into place (e.g., a slot which accepts a pin on ultrasound transducer/probe 234 when ultrasound transducer/probe 234 is rotated). In some embodiments, ultrasound board 232 includes multiple transducer/probe socket interfaces 238 to allow the connection of multiple socket type ultrasound transducers/probes 187.

In some embodiments, ultrasound board 232 also includes one or more transducer/probe pin interfaces 236. Transducer/probe pin interface 236 enables an ultrasound transducer/probe 234 with a pin type connector to interface with ultrasound board 232. Transducer/probe pin interface 236 may include circuitry and/or hardware connecting ultrasound transducer/probe 234 to ultrasound board 232 for the transfer of electrical power and/or data. Transducer/probe pin interface 236 may include hardware which locks ultrasound transducer/probe 234 into place. In some embodiments, ultrasound transducer/probe 234 is locked into place with locking lever system 120. In some embodiments, ultrasound board 232 includes multiple transducer/probe pin interface 236 to allow the connection of multiple pin type ultrasound transducers/probes 234. In such cases, portable ultrasound system 100 may include one or more locking lever systems 120. In further embodiments, ultrasound board 232 may include interfaces for additional types of transducer/probe connections.

With continued reference to FIG. 2, some embodiments of main circuit board 200 include display interface 240. Display interface 240 may include connections which enable communication between components of main circuit board 200 and display device hardware. For example, display interface 240 may provide a connection between main circuit board 200 and a liquid crystal display, a plasma display, a cathode ray tube display, a light emitting diode display, and/or a display controller or graphics processing unit for the proceeding or other types of display hardware. In some embodiments, the connection of display hardware to main circuit board 200 by display interface 240 allows a processor or dedicated graphics processing unit on main circuit board 200 to control and/or send data to display hardware. Display interface 240 may be configured to send display data to display device hardware in order to produce an image. In some embodiments, main circuit board 200 includes multiple display interfaces 240 for multiple display devices (e.g., three display interfaces 240 connect three displays to main circuit board 200). In other embodiments, one display interface 240 may connect and/or support multiple displays. In one embodiment, three display interfaces 240 couple touchpad 170, touchscreen 180, and main screen 190 to main circuit board 200.

In further embodiments, display interface 240 may include additional circuitry to support the functionality of attached display hardware or to facilitate the transfer of data between display hardware and main circuit board 200. For example, display interface 240 may include controller circuitry, a graphics processing unit, video display controller, etc. In some embodiments, display interface 240 may be a SOC or other integrated system which allows for displaying images with display hardware or otherwise controlling display hardware. Display interface 240 may be coupled directly to main circuit board 200 as either a removable package or embedded package. Processing circuit 210 in conjunction with one or more display interfaces 240 may display images on one or more of touchpad 170, touchscreen 180, and main screen 190.

Referring back to FIG. 1A, in some embodiments, portable ultrasound system 100 includes one or more pin type ultrasound probe interfaces 122. Pin type ultrasound interface 122 may allow an ultrasound probe to connect to an ultrasound board 232 included in ultrasound system 100. For example, an ultrasound probe connected to pin type ultrasound interface 122 may be connected to ultrasound board 232 via transducer/probe pin interface 236. In some embodiments, pin type ultrasound interface 122 allows communication between components of portable ultrasound system 100 and an ultrasound probe. For example, control signals may be provided to the transducer probe 112 (e.g., controlling the ultrasound emissions of the probe) and data may be received by ultrasound system 100 from the probe (e.g., imaging data).

In some embodiments, ultrasound system 100 may include locking lever system 120 for securing an ultrasound probe. For example, an ultrasound probe may be secured in pin type ultrasound probe interface 122 by locking lever system 120.

In further embodiments, ultrasound system 100 includes one or more socket type ultrasound probe interfaces 124. Socket type ultrasound probe interfaces 124 may allow a socket type ultrasound probe to connect to an ultrasound board 232 included in ultrasound system 100. For example, an ultrasound probe connected to socket type ultrasound probe interface 124 may be connected to ultrasound board 232 via transducer/probe socket interface 238. In some embodiments, socket type ultrasound probe interface 124 allows communication between components of portable ultrasound system 100 and other components included in or connected with portable ultrasound system 100. For example, control signals may be provided to an ultrasound probe (e.g., controlling the ultrasound emissions of the probe) and data may be received by ultrasound system 100 from the probe (e.g., imaging data).

Figure 3A:
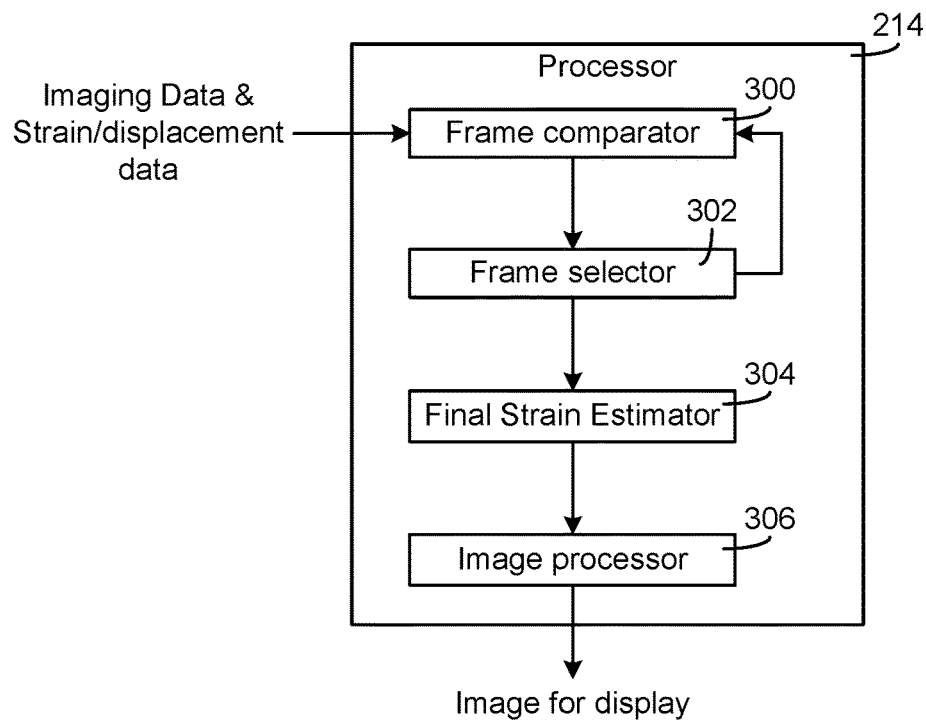
FIG. 3A is a block diagrams illustrating the processor of FIG. 2 in greater detail, according to exemplary embodiments.

Referring now to FIG. 3A, a block diagram of illustrating processor 214 is shown, according to an exemplary embodiment. Processor 214 may include a frame comparator 300, a frame selector 302, a final strain estimator 304 and image processor 306. Processor 214 may also include other standard image processing components (e.g. an analog to digital converter, an amplifier, a converter, a receiver, etc.).

Frame comparator 300 compares data from a single ultrasound frame comparison set with a plurality of ultrasound frame comparison sets. For example, frame one may be paired with frames two through ten, individually, with each set is being compared to the other sets (e.g. set containing frames one and two is compared to set containing frames one and three, etc.). The plurality of frames to compare to could be user defined. In some embodiments, the plurality of frames may be based on the number of frames in a cycle. In other embodiments, the plurality of frames may be based on the frame rate. The plurality of frames may be based on other criteria. In some embodiments, the plurality of frames is dynamic and adaptive. In other embodiment, the plurality of frames is different for different frames. The frame comparison sets may be compared based on mean strain. In some embodiments, the frame comparison sets may be compared based on SNR. In other embodiments, the frame comparison sets are compared based on a combination of mean strain and SNR. The frame comparator 300 includes the necessary electronics for computing or determining the criteria comparison is based on. The frame comparator 300 performs the comparison for all frame comparison sets in a designated segment of data. The designated segment of data could be the entire imaging time. In some embodiments, the designated segment could be one cycle of displacement (e.g. force applied and removed). In other embodiments, the designated segment could be a certain amount of frames passed. In yet some embodiments, the designated segment could be a certain amount of time passed. Once the frame comparator 300 has passed the designated segment, the frame comparator 300 may become passive.

Frame selector 302 selects a frame comparison set. A frame comparison set is two frames that were compared. For example, the selected frame comparison set for frame one could be frame one and frame five. The frame selector 302 may select the frame comparison set based on frames with adequate mean strain. In some embodiments, the frame selector 302 may select the frame comparison set based on frames with the best SNR. In yet some embodiments, the frame selector 302 may select the frame comparison set based on frames with mean strain in comparison to a desired strain (e.g. higher than, less than, within the range of, closest to, closest to but not exceeding, etc). The desired strain may be a minimum value, a maximum value, an average, a range, or another statistical measure. The desired strain may be user defined. In some embodiments, the desired strain may be based on previous data and/or results. In other embodiments, the frame selector 302 may select the frame comparison set based on a weighted system taking several aspects into consideration. In other embodiments, the frame selector 302 selects the frame comparison sets based on previous frame selections without frame comparator 300 comparing frames (e.g. when the frame comparator is passive after the designated segment is reached). The frame selector 302 may also use the frame comparison set data to predict a periodicity of motion. In some embodiments, the frame selector 302 may use a history of mean displacement over time to predict the periodicity of motion. Predicting the periodicity of motion allows the frame selector to use previous frame comparison sets for new data coming in. This reduces the processing time required to select the compared frames.

Final strain estimator 304 estimates the final strain for image processing. The final strain estimator 304 uses the frame comparison sets selected to estimate the strain. The strain estimator 304 may normalize the imaging data to estimate the strain. The final strain estimator 304 may use other techniques for determining a final strain estimation. By using the frame comparison sets to estimate the final strain, the elastography has dynamic persistence of displacement which reduces strain fluctuations, which cause poor image quality.

Image processor 306 uses the imaging data, and the final strain estimation, to process an elastography image. This may involve deformation analysis techniques, or other imaging techniques that allow elastography images to be created. The image processor may include other standard imaging components (e.g., an amplifier, a converter, a receiver, etc.).

Figure 3B:
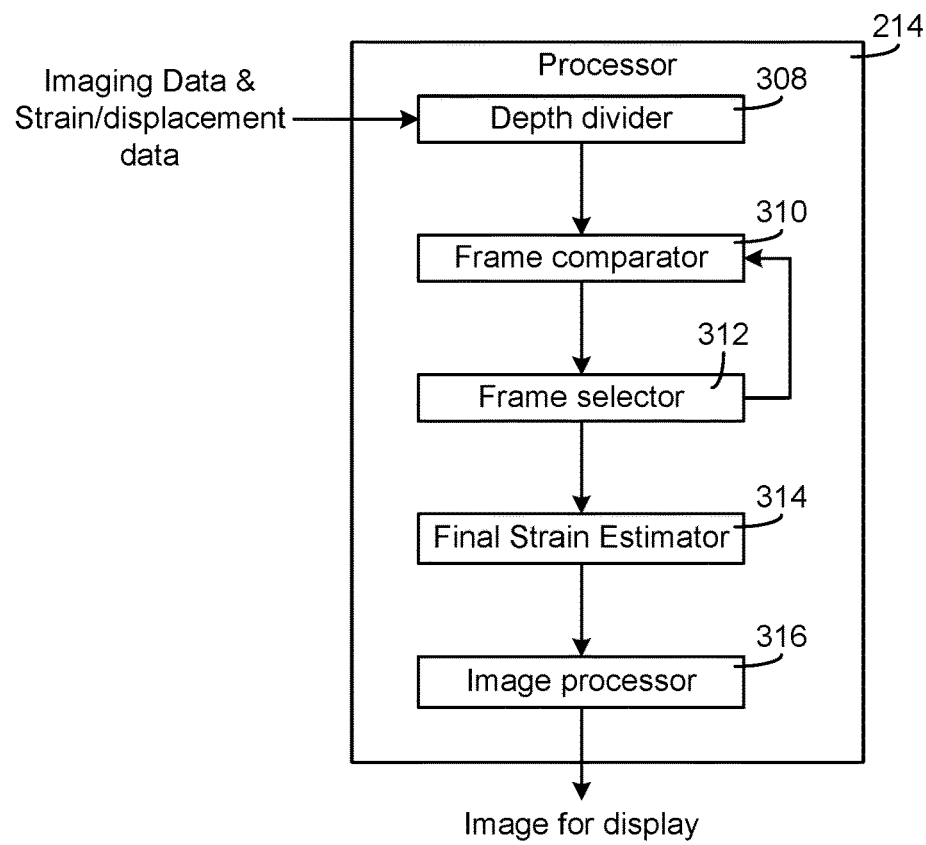
FIG. 3B is a block diagrams illustrating the processor of FIG. 2 in greater detail, showing depth variation, according to an exemplary embodiment.

Referring now to FIG. 3B, a block diagram of illustrating processor 214 is shown, according to an exemplary embodiment. Processor 214 includes depth divider 308, frame comparator 310, frame selector 312 and final strain estimator 314. Processor 214 may also include other standard imaging processing components.

Depth divider 308 receives the imaging data and divides each frame into sections based on depth. The depth divider 308 may divide the frame based on a first half and second half of depth. In other embodiments, the depth divider 308 may divide the frames into three depth sections. Any depth section classifications are considered within the scope of the disclosure. The depth divider 308 may divide the frames into sections based on user input. In some embodiments, the depth divider 308 may divide the frames into sections based on image quality. In other embodiments, the depth divider 308 may divide the frames into sections based on the strain decay at a given depth. The depth divider 308 may divide the frames into sections based on other image processing techniques.

Frame comparator 310 compares data from a single ultrasound frame comparison set with a plurality of ultrasound frame comparison sets, for a specified depth section. For example, frame five, depth section two, may be paired with depth section one of frames one through four, individually, with each set is being compared to the other sets (e.g., set containing frames one and three, depth section one, is compared to set containing frames two and three, depth section one, etc.). The plurality of frames to compare to could be user defined. In some embodiments, the plurality of frames may be based on the number of frames in a cycle. In other embodiments, the plurality of frames may be based on the frame rate. The plurality of frames may be based on other criteria. In some embodiments, the plurality of frames is dynamic and adaptive. In other embodiment, the plurality of frames is different for different frames. The frame comparison sets may be compared based on mean strain. In some embodiments, the frame comparison sets may be compared based on SNR. In other embodiments, the frame comparison sets are compared based on a combination of mean strain and SNR. The frame comparator 310 includes the necessary electronics for computing or determining the criteria comparison is based on. The frame comparator 310 performs the comparison for all frame comparison sets and all depth sections in a designated segment of data. The designated segment of data could be the entire imaging time. In some embodiments, the designated segment could be one cycle of displacement (e.g. force applied and removed). In other embodiments, the designated segment could be a certain amount of frames passed. In yet some embodiments, the designated segment could be a certain amount of time passed. Once the frame comparator 310 has passed the designated segment, the frame comparator 310 may become passive.

Frame selector 312 selects a frame comparison set for each frame, and each depth section in a given frame. A frame comparison set is two frames that were compared. For example, the selected frame comparison set for frame one could be frame one and frame five for the first depth section, and frame one and frame eight for the second depth section. The frame selector 312 may select the frame comparison set based on frames with adequate mean strain. In some embodiments, the frame selector 312 may select the frame comparison set based on frames with the best SNR. In yet some embodiments, the frame selector 312 may select the frame comparison set based on frames with mean strain in comparison to a desired strain (e.g. higher than, less than, within the range of, closest to, closest to but not exceeding, etc). The desired strain may be a minimum value, a maximum value, an average, a range, or another statistical measure. The desired strain may be user defined. In some embodiments, the desired strain may be based on previous data and/or results. In other embodiments, the frame selector 312 may select the frame comparison set based on a weighted system taking several aspects into consideration. In other embodiments, the frame selector 312 selects the frame comparison sets based on previous frame selections without frame comparator 310 comparing frames (e.g. when the frame comparator is passive after the designated segment is reached). The frame selector 312 may also use the frame comparison set data to predict a periodicity of motion. In some embodiments, the frame selector 312 may use a history of mean displacement over time to predict the periodicity of motion. Predicting the periodicity of motion allows the frame selector to use previous frame comparison sets for new data coming in. This reduces the processing time required to select the compared frames.

Final strain estimator 314 estimates the final strain for image processing. The final strain estimator 314 uses the frame comparison sets selected for each frame and each depth section to estimate the strain. The strain estimator 314 may normalize the imaging data to estimate the strain. The strain estimator 314 may normalize a subset of depth sections. The strain estimator 314 may normalize all depth sections. The final strain estimator 314 may use other techniques for determining a final strain estimation. By using the frame comparison sets to estimate the final strain, the elastography has dynamic persistence of displacement which reduces strain fluctuations, which cause poor image quality.

Image processor 316 uses the imaging data, and the final strain estimation, to process an elastography image. This may involve deformation analysis techniques, or other imaging techniques that allow elastography images to be created. The image processor may include other standard imaging components (e.g., an amplifier, a converter, a receiver, etc.).

Figure 4:
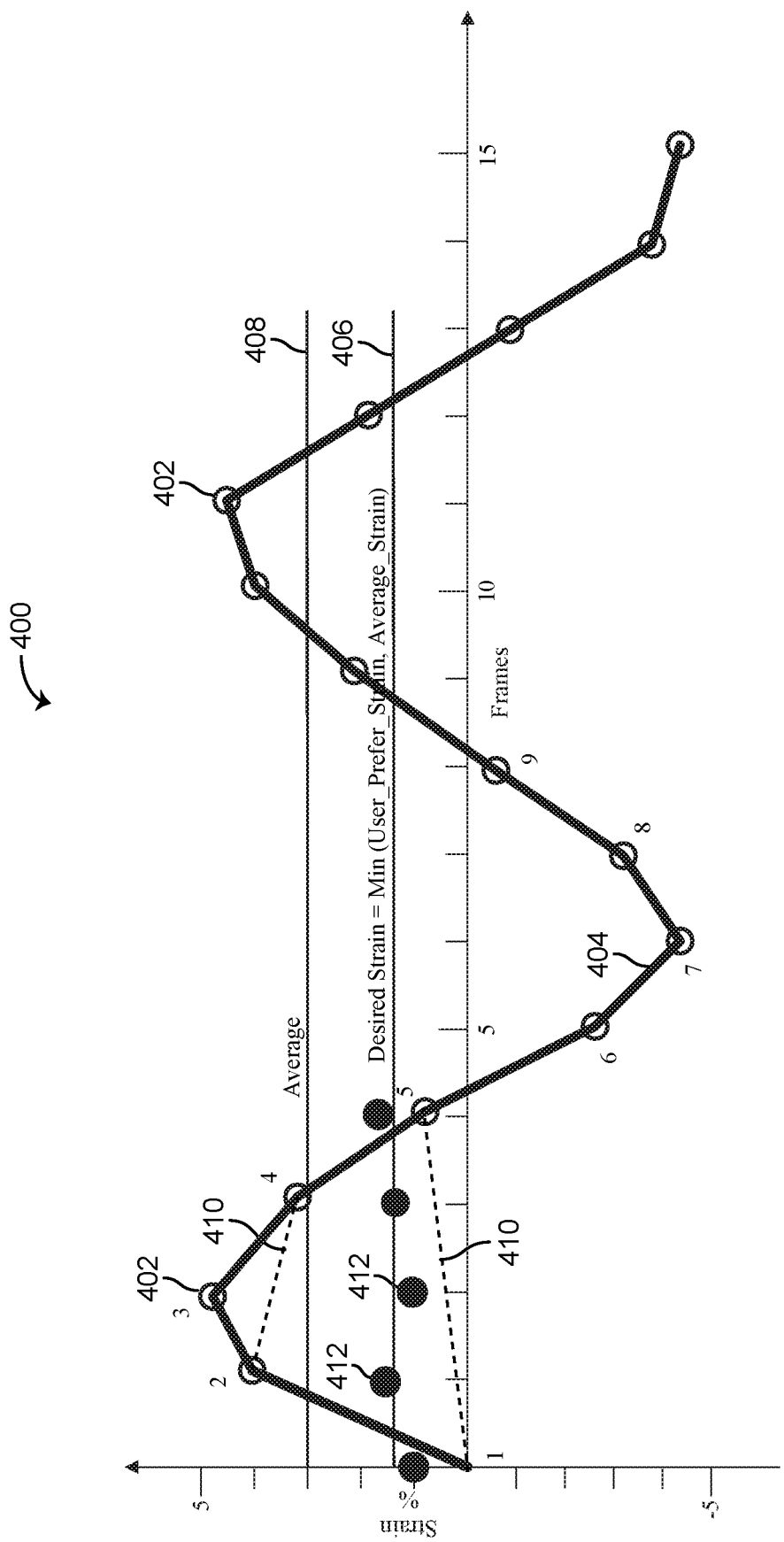
FIG. 4 is a graph of the frame comparison and selection of FIGS. 3A-3B, according to an exemplary embodiment.

Now referring to FIG. 4, a graph 400 of the frame comparison and selection of FIGS. 3A-3B, according to an exemplary embodiment, is shown. As the tissue is deformed and allowed to return to a normal state, frame by frame, the periodic motion of strain can be seen. The strain may be measured as a percent. The circles 402 at each frame represent the strain at that frame. The line 404 connecting all the points shows the change from one frame to the next, and as a whole shows the periodicity of motion. The desired strain 406 and average strain 408 are also included on the graph to show the target strain.

Referring now to FIGS. 5A and 5B, tables of the frame comparisons and frame comparison sets of FIGS. 3A and 3B are shown, according to an exemplary embodiment. In the first column, frames four and five are shown being compared to frames zero through three and one through four, respectively. In the second column, the mean strain in the tissue for the frames being compared is shown. For FIG. 5B, the mean strain in the first and second half depths are shown independently, as they are compared independently. The final column shows which frame comparison set was chosen for the given frame, based on the comparison of the frame sets. In FIG. 5B, the second half is normalized. This may be done to maintain a mean strength that is consistent between both halves. In some embodiments, the first half may be normalized. In some embodiments, all sections may be normalized. Any combination or subset of depth sections that are normalized is considered within the scope of the disclosure. While these tables show a method for comparison, they are just examples for visual aid and should not be considered limiting in any way.

Referring back to FIG. 4, the frame comparison set that was selected in FIG. 5A can be seen as the line 410, connecting frame one to frame five, and frame two to frame four. Just two selected comparison sets are shown, but any number of selected comparison sets could be represented on the graph. The resulting mean strain percent from the selected frame comparison set for the specified frame can be seen as dots 412. The mean strain may be used because with too much or too little strain, the image quality is not sufficient and is inconsistent. By comparing the frames and frame sets, the final strain estimation improves image quality.

Figure 6:
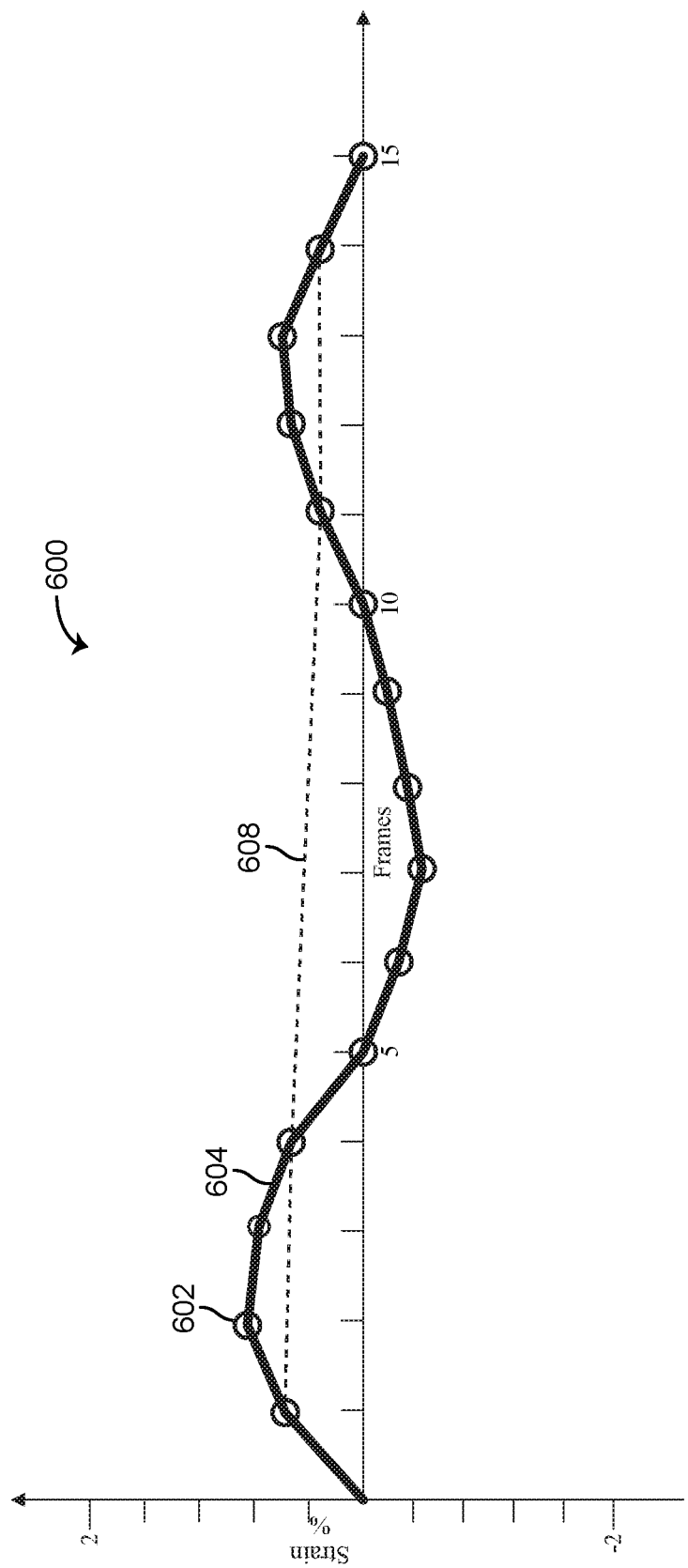
FIG. 6 is a graph of the frames and displacement after time-varying frame selection has occurred, according to an exemplary embodiment.

FIG. 6 is a graph 600 of the frames and displacement after time-varying frame selection has occurred, according to an exemplary embodiment. Dots 602 represent the final strain estimation (as percent displacement) for a given frame after frame comparison and calculating the final strain based on the selected frame comparison set. Line 604 connects these final strain estimations. While the strain is still periodic as the technician moves the probe up and down on the area of interest, using the frame comparison ensures strain estimations for each frame reside within a window of the desired strain, allowing for improved and consistent image quality, without dependence on the ultrasound operator maintaining consistent pressure. Line 608 shows the average final strain estimation across the frames. Even with the periodicity of motion, the average final strain estimation remains fairly constant, providing consistent, and improved, image quality.

Figure 7A:
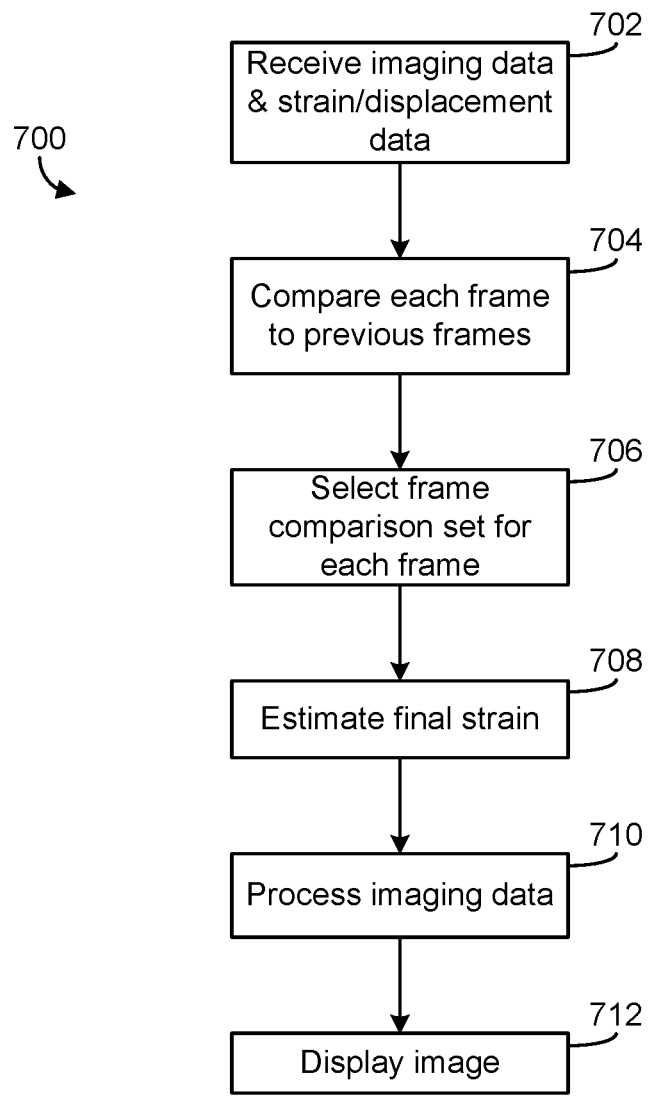
FIGS. 7A-7B are flowcharts of a process for time-varying frame selection in an ultrasound system, according to an exemplary embodiment.

FIG. 7A is a flowchart of a process 700 for time-varying frame selection in an ultrasound system, according to an exemplary embodiment. Process 700 may include receiving imaging and strain/displacement data (step 702), comparing each frame to previous frames (step 704), selecting a frame comparison set for each frame (step 706), estimating the final strain (708), processing the imaging data (step 710) and displaying the image (step 712).

Step 702 receives the imaging data and displacement/strain data from a transducer probe. The data could be raw data. In some embodiments, the data is preprocessed. Preprocessing could include A/D conversion, amplification, or other forms of image processing.

Step 704 is comparing data from a single ultrasound frame comparison set with a plurality of ultrasound frame comparison sets. For example, frame five may be paired with frames one through four, individually, with each set is being compared to the other sets (e.g. set containing frames five and two is compared to set containing frames five and three, etc.). The plurality of frames to compare to could be user defined. In some embodiments, the plurality of frames may be based on the number of frames in a cycle. In other embodiments, the plurality of frames may be based on the frame rate. The plurality of frames may be based on other criteria. In some embodiments, the plurality of frames is dynamic and adaptive. In other embodiments, the plurality of frames is different for different frames. The frame comparison sets may be compared based on mean strain. In some embodiments, the frame comparison sets may be compared based on SNR. In other embodiments, the frame comparison sets are compared based on a combination of mean strain and SNR. Step 704 includes computing or determining the criteria the comparison is based on. Step 704 may include comparing all frames in a designated segment of data. The designated segment of data could be the entire imaging time. In some embodiments, the designated segment could be one cycle of displacement (e.g. force applied and removed). In other embodiments, the designated segment could be a certain amount of frames. In yet some embodiments, the designated segment could be a certain amount of time passed.

Step 706 selects a frame comparison set. A frame comparison set is two frames that were compared. For example, the selected frame comparison set for frame one could be frame one and frame five. Step 706 may be selecting the frame comparison set based on frames with adequate mean strain. In some embodiments, step 706 may be selecting the frame comparison set based on frames with the best SNR. In yet some embodiments, step 706 may be selecting the frame comparison set based on frames with mean strain in comparison to a desired strain (e.g. higher than, less than, within the range of, closest to, closest to but not exceeding, etc). The desired strain may be a minimum value, a maximum value, an average, a range, or another statistical measure. The desired strain may be user defined. In some embodiments, the desired strain may be based on previous data and/or results. In other embodiments, step 706 may be selecting the frame comparison set based on a weighted system taking several aspects into consideration. Step 706 may also include using the frame comparison set data to predict a periodicity of motion. In some embodiments, step 706 may include using a history of mean displacement over time to predict the periodicity of motion. Predicting the periodicity of motion allows the frame selector to use previous frame comparison sets for new data coming in. This reduces the processing time required to select the compared frames.

Step 708 estimates the final strain for image processing. Step 708 uses the frame comparison sets selected to estimate the strain. Step 708 may include normalizing the imaging data to estimate the strain. Step 708 may involve other techniques for determining a final strain estimation. By using the frame comparison sets to estimate the final strain, the elastography has dynamic persistence of displacement which reduces strain fluctuations, which cause poor image quality.

Step 710 uses the imaging data and the final strain estimation, to process an elastography image. This may involve deformation analysis techniques, or other imaging techniques that allow elastography images to be created. The image processing may include other standard imaging computational steps (e.g. analog to digital converting, amplifying, converting, receiving, etc.).

Step 712 displays the resulting elastography image on a screen for the user to see. The image may be displayed on touchpad 170, touchscreen 180, and/or main screen 190.

Figure 7B:
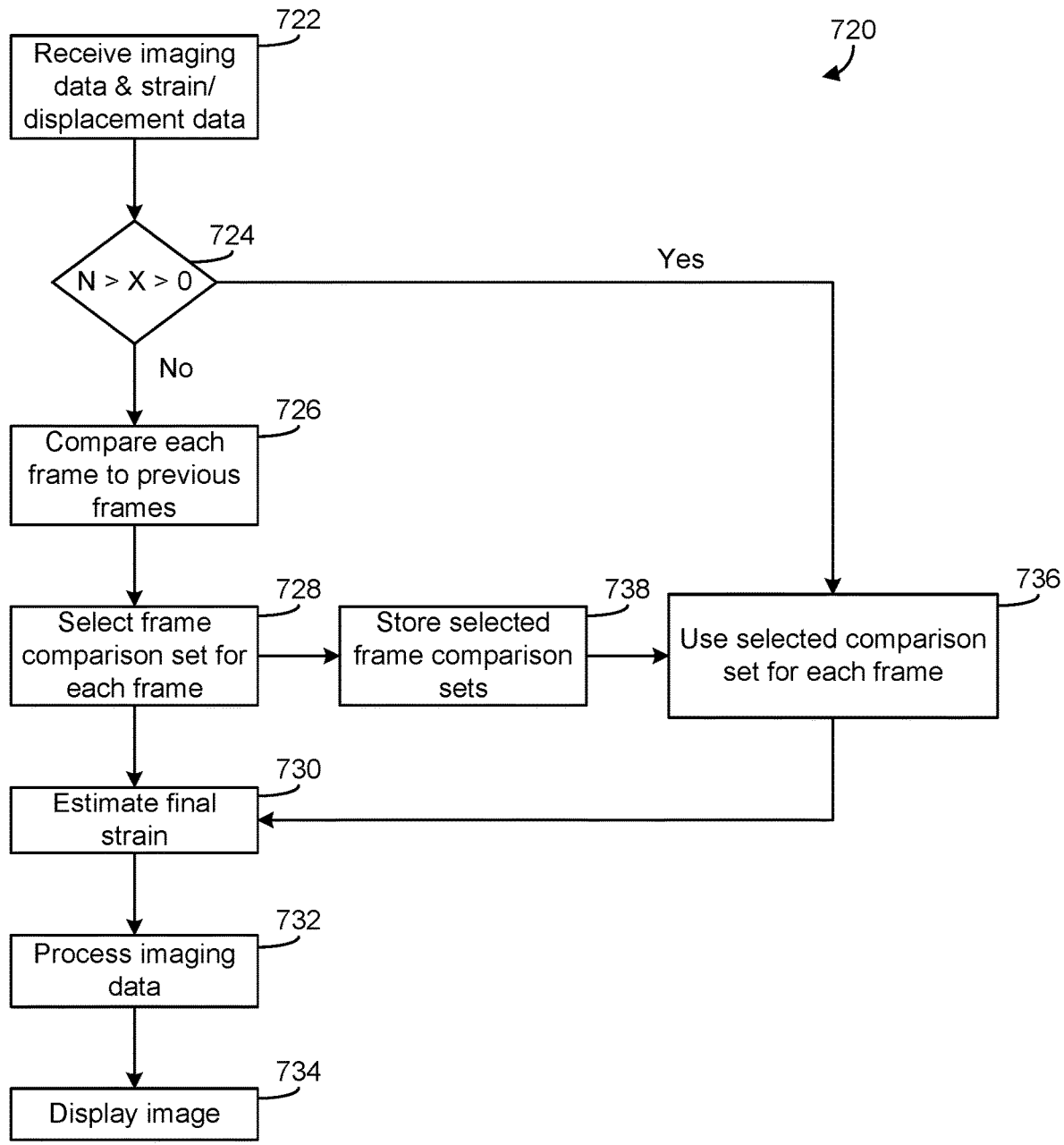

FIG. 7B is a flowchart of a process 720 for time-varying frame selection with feedback in an ultrasound system, according to an exemplary embodiment. Process 700 may include receiving imaging and strain/displacement data (step 722), making a decision (step 724), comparing each frame to previous frames (step 726), selecting a frame comparison set for each frame (step 728), storing the selected frame comparison set (step 738), estimating the final strain (730), processing the imaging data (step 732), and displaying the image (step 734); and the alternate path includes the feedback for selecting a comparison frame set (step 736).

Step 722 receives the imaging data and displacement/strain data from a transducer probe. The data could be raw data. In some embodiments, the data is preprocessed. Preprocessing could include A/D conversion, amplification, or other form of image processing.

Step 724 is a decision step. Step 724 compares N to X, and X to zero, for decision making. If X is greater than N, steps 726-734, 738 are followed. If X is not greater than N, but greater than zero, steps 736, 730, 732 and 734 are followed. In some embodiments, X and N represent cycles, where X is the count of the current cycle, and N is a specified cycle number. In other embodiments, X is a frame counter, and N is a specified number of frames. In yet some embodiments, X is a time counter, and N is a specified amount of time. X and N may be any type of system that will allow the process to know when a certain point is reached and the alternate path should be used. N may be user defined. In some embodiments, N may be determined based on previous data and/or results.

If X is greater than N, step 726 compares data from a single ultrasound frame comparison set with a plurality of ultrasound frame comparison sets. For example, frame five may be paired with frames one through four, individually, with each set is being compared to the other sets (e.g. set containing frames five and two is compared to set containing frames five and three, etc.). The plurality of frames to compare to could be user defined. In some embodiments, the plurality of frames may be based on the number of frames in a cycle. In other embodiments, the plurality of frames may be based on the frame rate. The plurality of frames may be based on other criteria. In some embodiments, the plurality of frames is dynamic and adaptive. In other embodiment, the plurality of frames is different for different frames. The frame comparison sets may be compared based on mean strain. In some embodiments, the frame comparison sets may be compared based on SNR. In other embodiment, the frame comparison sets are compared based on a combination of mean strain and SNR. Step 726 may include computing or determining the criteria the comparison is based on. Step 726 compares all frames in a designated segment of data. The designated segment of data could be the entire imaging time. In some embodiments, the designated segment could be one cycle of displacement (e.g. force applied and removed). In other embodiments, the designated segment could be a certain amount of frames. In yet some embodiments, the designated segment could be a certain amount of time passed.

Step 728 selects a frame comparison set. A frame comparison set is two frames that were compared. For example, the selected frame comparison set for frame one could be frame one and frame five. Step 728 may be selecting the frame comparison set based on frames with adequate mean strain. In some embodiments, step 728 may be selecting the frame comparison set based on frames with the best SNR. In yet some embodiments, step 728 may be selecting the frame comparison set based on frames with mean strain in comparison to a desired strain (e.g. higher than, less than, within the range of, closest to, closest to but not exceeding, etc). The desired strain may be a minimum value, a maximum value, an average, a range, or another statistical measure. The desired strain may be user defined. In some embodiments, the desired strain may be based on previous data and/or results. In other embodiments, step 728 may be selecting the frame comparison set based on a weighted system taking several aspects into consideration. Step 728 may include using the frame comparison set data to predict a periodicity of motion. In some embodiments, step 728 may include using a history of mean displacement over time to predict the periodicity of motion. Predicting the periodicity of motion allows the frame selector to use previous frame comparison sets for new data coming in. This reduces the processing time required to select the compared frames. Two steps follow step 728, storing the selected frame comparison set (step 738) and estimating the final strain (step 730).

Step 738 stores the selected frame comparison sets. By storing the selected frame comparison sets, frames do not need to be compared to previous frames after the counting threshold (N>X>0) is satisfied. This decreases processing time.

If X is not greater than N, step 736 involves using the stored selected frame comparison set to estimate the final strain in step 730, using the new data. For example, for the first cycle, all the frames will be compared to previous frames and frame comparison sets will be selected and stored (e.g. frame one and frame five is the selected frame comparison set for frame five). Once the second cycle is entered, frame five of cycle two will not be compared to any frames, it will automatically have frame one as its frame comparison set for estimating the final strain.

Regardless of which path is taken, step 730 estimates the final strain for image processing. Step 730 may involve using the frame comparison sets selected to estimate the strain. Step 730 may include taking the average strain between the two frames to estimate final strain. In some embodiments, step 730 may include using a weighted average of the two frames to estimate the final strain. Step 730 may include normalizing the imaging data to estimate the strain. Step 730 may include using other techniques for determining a final strain estimation. By using the frame comparison sets to estimate the final strain, the elastography has dynamic persistence of displacement which reduces strain fluctuations, which cause poor image quality.

Step 732 includes using the imaging data, and the final strain estimation, to process an elastography image. This may involve deformation analysis techniques, or other imaging techniques that allow elastography images to be created. The image processing may include other standard imaging computations (e.g. analog to digital converting, amplifying, converting, receiving, etc.).

Step 734 displays the resulting elastography image on a screen for the user to see. The image may be displayed on touchpad 170, touchscreen 180, and/or main screen 190.

Figure 8A:
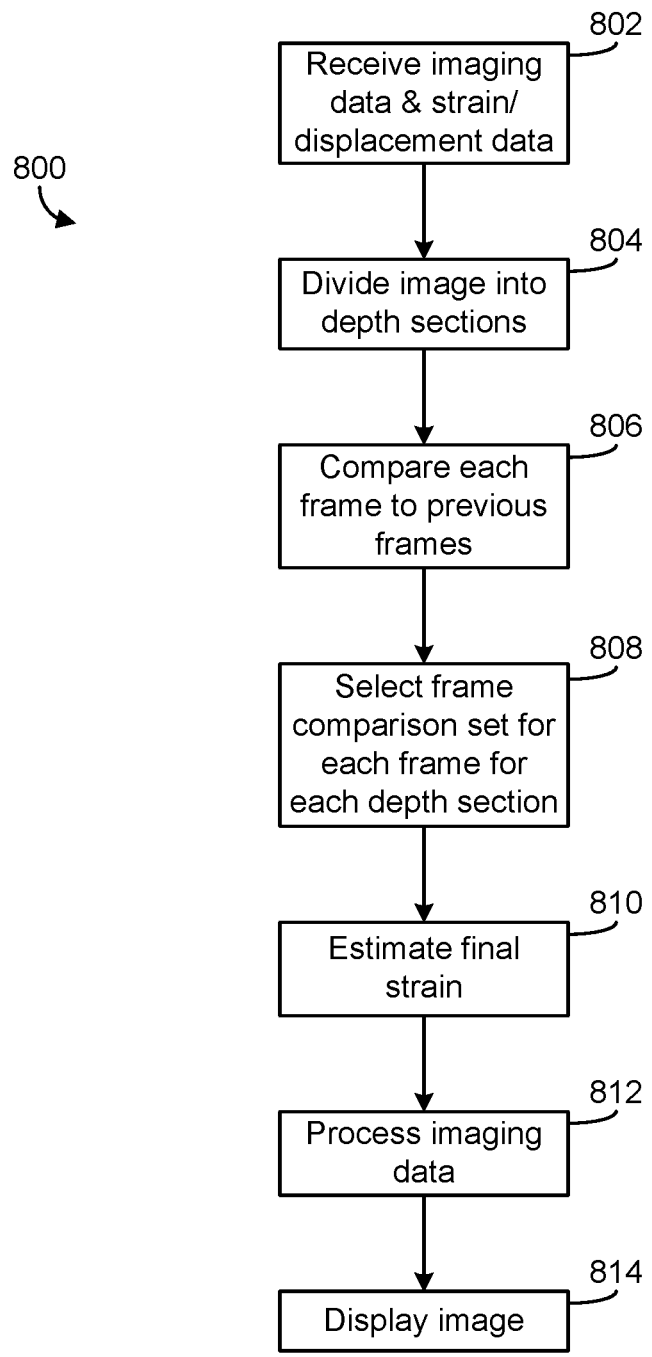
FIG. 8A-8B are flowcharts of a process for time-varying frame selection with depth variation in an ultrasound system, according to an exemplary embodiment.

FIG. 8A is a flowchart of a process 800 for time-varying frame selection with depth variation in an ultrasound system, shown in greater detail, according to an exemplary embodiment. Process 800 may include receiving imaging and strain/displacement data (step 802), dividing the image into depth sections (step 804), comparing each frame to previous frames (step 806), selecting a frame comparison set for each frame for each depth section (step 808), estimating the final strain (810), processing the imaging data (step 812) and displaying the image (step 814).

Step 802 is receiving the imaging data and displacement/strain data from a transducer probe. The data could be raw data. In some embodiments, the data is preprocessed. Preprocessing could include A/D conversion, amplification, or other form of image processing.

Step 804 is dividing the images into depth sections. Step 804 may include dividing the frame based on a first half and second half of depth. In other embodiments, step 804 may include dividing the frames into three depth sections. Any depth section classifications are considered within the scope of the disclosure. Step 804 may include dividing the frames into sections based on user input. In some embodiments, step 804 may include dividing the frames into sections based on image quality. In other embodiment, step 804 may include dividing the frames into sections based on the strain decay at a given depth. Step 804 may include dividing the frames into sections based on other image processing techniques.

Step 806 is comparing data from a single ultrasound frame comparison set with a plurality of ultrasound frame comparison sets, for a specified depth section. For example, frame one, depth section one, may be paired with depth section one of frames two through ten, individually, with each set is being compared to the other sets (e.g. set containing frames one and two, depth section one, is compared to set containing frames one and three, depth section one, etc.). The plurality of frames to compare to could be user defined. In some embodiments, the plurality of frames may be based on the number of frames in a cycle. In other embodiments, the plurality of frames may be based on the frame rate. The plurality of frames may be based on other criteria. In some embodiments, the plurality of frames is dynamic and adaptive. In other embodiment, the plurality of frames is different for different frames. The frame comparison sets may be compared based on mean strain. In some embodiments, the frame comparison sets may be compared based on SNR. In other embodiment, the frame comparison sets are compared based on a combination of mean strain and SNR. Step 806 includes computing or determining the criteria the comparison is based on. Step 806 includes comparing all frames and all depth sections in a designated segment of data. The designated segment of data could be the entire imaging time. In some embodiments, the designated segment could be one cycle of displacement (e.g. force applied and removed). In other embodiments, the designated segment could be a certain amount of frames. In yet some embodiments, the designated segment could be a certain amount of time passed.

Step 808 is selecting a frame comparison set for each frame for each depth section in a given frame. A frame comparison set is two frames that were compared. For example, the selected frame comparison set for frame one could be frame one and frame five for the first depth section, and frame one and frame eight for the second depth section. Step 808 may include selecting the frame comparison set based on frames with adequate mean strain. In some embodiments, step 808 may include selecting the frame comparison set based on frames with the best SNR. In yet some embodiments, step 808 includes selecting the frame comparison set based on frames with mean strain in comparison to a desired strain (e.g. higher than, less than, within the range of, closest to, closest to but not exceeding, etc). The desired strain may be a minimum value, a maximum value, an average, a range, or another statistical measure. The desired strain may be user defined. In some embodiments, the desired strain may be based on previous data and/or results. In other embodiments, step 808 may include selecting the frame comparison set based on a weighted system taking several aspects into consideration. Step 808 may include using the frame comparison set data predict a periodicity of motion. In some embodiments, step 808 may include using a history of mean displacement over time to predict the periodicity of motion. Predicting the periodicity of motion allows the frame selector to use previous frame comparison sets for new data coming in. This reduces the processing time required to select the compared frames.

Step 810 is estimating the final strain for image processing. Step 810 may be using the frame comparison sets selected for each frame and each depth section to estimate the strain. Step 810 may include normalizing the imaging data to estimate the strain. Step 810 may include normalizing a subset of depth sections. Step 810 may include normalizing all depth sections. In some embodiments, step 810 includes computing a mean strain for estimating the final strain. In other embodiments, step 810 includes computing a weighted average for estimating the final strain. Step 810 may include using other techniques for determining a final strain estimation. By using the frame comparison sets to estimate the final strain, the elastography has dynamic persistence of displacement which reduces strain fluctuations, which cause poor image quality.

Step 812 includes using the imaging data, and the final strain estimation, to process an elastography image. This may involve deformation analysis techniques, or other imaging techniques that allow elastography images to be created. The image processing may include other standard imaging computations (e.g. analog to digital converting, amplifying, converting, receiving, etc.).

Step 814 is displaying the resulting elastography image on a screen for the user to see. The image may be displayed on touchpad 170, touchscreen 180, and/or main screen 190.

Figure 8B:
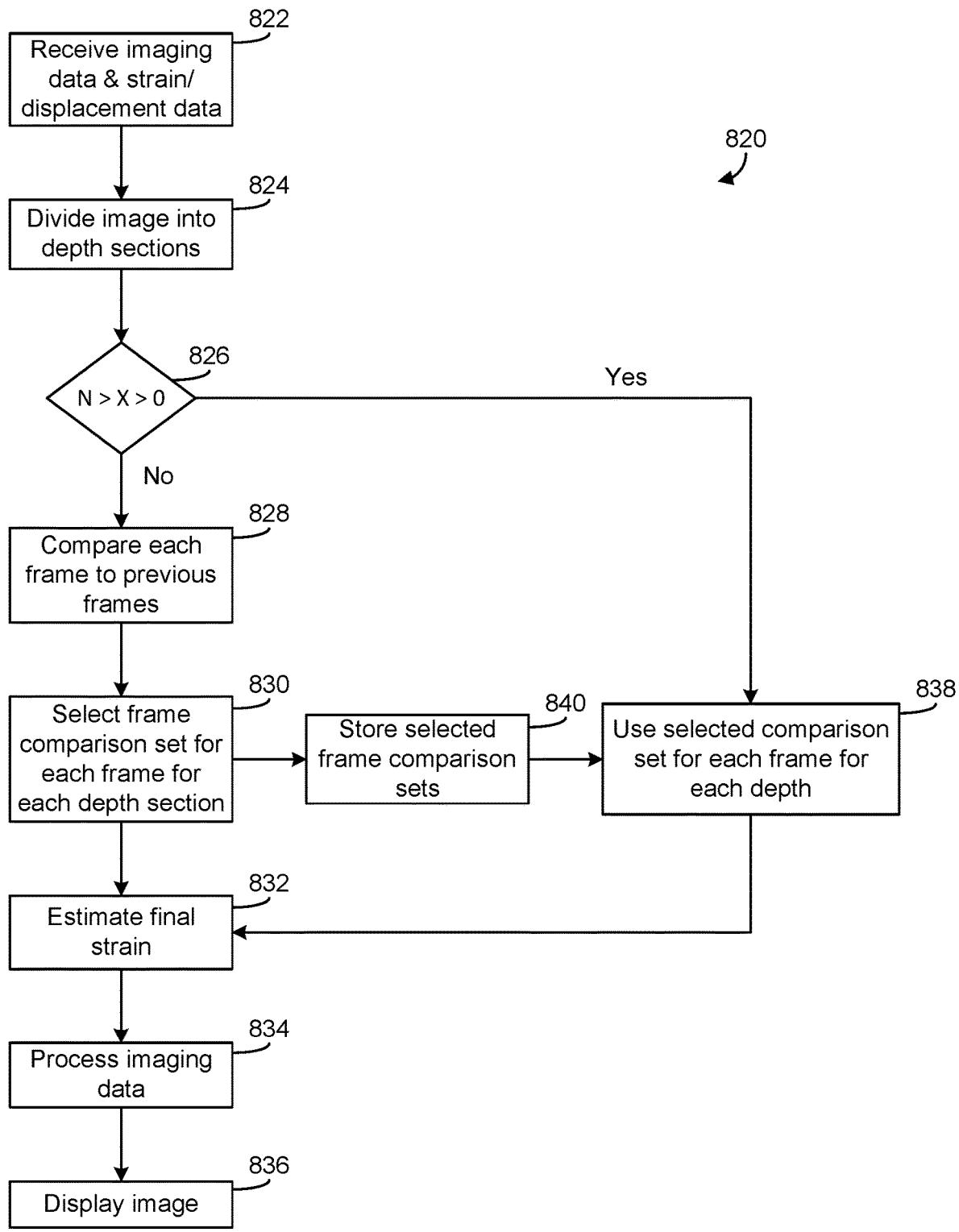

FIG. 8B is a flowchart of a process 820 for time-varying frame selection with feedback in an ultrasound system, according to an exemplary embodiment. Process 820 may include receiving imaging and strain/displacement data (step 822), dividing the image into depth sections (step 824), making a decision (step 826), comparing each frame to previous frames (step 828), selecting a frame comparison set for each frame (step 830), storing the selected frame comparison set (step 840), estimating the final strain (step 832), processing the imaging data (step 834), and displaying the image (step 836); and the alternate path includes the feedback for selecting a comparison frame set (step 838).

Step 822 is receiving the imaging data and displacement/strain data from a transducer probe. The data could be raw data. In some embodiments, the data is preprocessed. Preprocessing could include A/D conversion, amplification, or other form of image processing.

Step 824 is dividing the images into depth sections. Step 824 may include dividing the frame based on a first half and second half of depth. In other embodiments, step 824 may include dividing the frames into three depth sections. Any depth section classifications are considered within the scope of the disclosure. Step 824 may include dividing the frames into sections based on user input. In some embodiments, step 824 may include dividing the frames into sections based on image quality. In other embodiment, step 824 may include dividing the frames into sections based on the strain decay at a given depth. Step 824 may include dividing the frames into sections based on other image processing techniques.

Step 826 is a decision step. Step 826 compares X to N, and X to zero, for decision making. If X is greater than N, steps 828-836, 840 are followed. If X is not greater than N, steps 838, 832, 834 and 836 are followed. In some embodiments, X and N represent cycles, where X is the count of the current cycle, and N is a specified cycle number. In other embodiments, X is a frame counter, and N is a specified number of frames. In yet some embodiments, X is a time counter, and N is a specified amount of time. X and N may be any type of system that will allow the process to know when a certain point is reached and the alternate path should be used. N may be user defined. In some embodiments, N may be determined based on previous data and/or results.

If X is greater than N, step 828 is comparing data from a single ultrasound frame comparison set with a plurality of ultrasound frame comparison sets, for a specified depth section. For example, frame five, depth section one, may be paired with depth section one of frames one through four, individually, with each set is being compared to the other sets (e.g. set containing frames one and five, depth section one, is compared to set containing frames three and five, depth section one, etc.). The plurality of frames to compare to could be user defined. In some embodiments, the plurality of frames may be based on the number of frames in a cycle. In other embodiments, the plurality of frames may be based on the frame rate. The plurality of frames may be based on other criteria. In some embodiments, the plurality of frames is dynamic and adaptive. In other embodiment, the plurality of frames is different for different frames. The frame comparison sets may be compared based on mean strain. In some embodiments, the frame comparison sets may be compared based on SNR. In other embodiment, the frame comparison sets are compared based on a combination of mean strain and SNR. Step 828 includes computing or determining the criteria the comparison is based on. Step 828 includes comparing all frames and all depth sections in a designated segment of data. The designated segment of data could be the entire imaging time. In some embodiments, the designated segment could be one cycle of displacement (e.g. force applied and removed). In other embodiments, the designated segment could be a certain amount of frames. In yet some embodiments, the designated segment could be a certain amount of time passed.

Step 830 is selecting a frame comparison set for each frame, and each depth section in a given frame. A frame comparison set is two frames that were compared. For example, the selected frame comparison set for frame one could be frame one and frame five for the first depth section, and frame one and frame eight for the second depth section. Step 830 may include selecting the frame comparison set based on frames with adequate mean strain. In some embodiments, step 830 may include selecting the frame comparison set based on frames with the best SNR. In yet some embodiments, step 830 includes selecting the frame comparison set based on frames with mean strain in comparison to a desired strain (e.g. higher than, less than, within the range of, closest to, closest to but not exceeding, etc). The desired strain may be a minimum value, a maximum value, an average, a range, or another statistical measure. The desired strain may be user defined. In some embodiments, the desired strain may be based on previous data and/or results. In other embodiments, step 830 may include selecting the frame comparison set based on a weighted system taking several aspects into consideration. Step 830 may include using the frame comparison set data to predict a periodicity of motion. In some embodiments, step 830 may include using a history of mean displacement over time to predict the periodicity of motion. Predicting the periodicity of motion allows the frame selector to use previous frame comparison sets for new data coming in. This reduces the processing time required to select the compared frames.

Step 840 is storing the selected frame comparison sets. By storing the selected frame comparison sets, frames do not need to be compared to previous frames after the counting threshold (N>X>0) is satisfied. This decreases processing time.

If X is not greater than N, step 838 uses the stored selected frame comparison set to estimate the final strain in step 832, using the new data. For example, for the first cycle, all the frames will be compared to previous frames and frame comparison sets will be selected and stored (e.g. frame one and frame five is the selected frame comparison set for frame five). Once the second cycle is entered, frame five of cycle two will not be compared to any frames, it will automatically have frame one as its frame comparison set for estimating the final strain.

Regardless of which path is taken, step 832 is estimating the final strain for image processing. Step 832 may be using the frame comparison sets selected for each frame and each depth section to estimate the strain. Step 832 may include normalizing the imaging data to estimate the strain. Step 832 may include normalizing a subset of depth sections. Step 832 may include normalizing all depth sections. In some embodiments, step 832 includes computing a mean strain for estimating the final strain. In other embodiments, step 832 includes computing a weighted average for estimating the final strain. Step 832 may include using other techniques for determining a final strain estimation. By using the frame comparison sets to estimate the final strain, the elastography has dynamic persistence of displacement which reduces strain fluctuations, which cause poor image quality.

Step 834 includes using the imaging data, and the final strain estimation, to process an elastography image. This may involve deformation analysis techniques, or other imaging techniques that allow elastography images to be created. The image processing may include other standard imaging computations (e.g. analog to digital converting, amplifying, converting, receiving, etc.).

Step 836 is displaying the resulting elastography image on a screen for the user to see. The image may be displayed on touchpad 170, touchscreen 180, and/or main screen 190.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. An ultrasound processing system for elastography comprising:
    an ultrasound interface connector that receives ultrasound imaging information including a plurality of frames including at least a first frame, a second frame previous to the first frame, and a third frame previous to the first frame; and
    processing electronics coupled to the ultrasound interface connector, wherein the processing electronics:
    divide each of the plurality of frames into a plurality of sections, wherein each of the plurality of frames is divided into the plurality of sections based on a strain decay at a given depth;
    for each particular section of the plurality of sections of the first frame of the plurality of frames:
        generate a plurality of comparison sets and corresponding selection values including at least a first comparison set having a corresponding selection value based on the particular section of the first frame of the plurality of frames and the particular section of the second frame of the plurality of frames and a second comparison set having a corresponding selection value based on the particular section of the first frame of the plurality of frames and the particular section of the third frame of the plurality of frames, each selection value including at least one of a displacement or a strain;
        select, responsive to generating the plurality of comparison sets, a single comparison set from the plurality of comparison sets based on the corresponding selection values of each of the plurality of comparison sets; and
        assign the selection value of the selected single comparison set to the particular section of the first frame; and
    generate an image based on the plurality of frames using the selected single comparison set and the assigned selection value for each section of the plurality of sections of the first frame.

2. The ultrasound processing system of claim 1, wherein the processing electronics use multi-frame displacement estimation for comparing frames.

3. The ultrasound processing system of claim 1, wherein each of the corresponding selection values includes a mean strain, and the processing electronics select the selected single comparison set by comparing the mean strain to a desired strain.

4. The ultrasound processing system of claim 1, wherein the processing electronics select the selected single comparison set having a highest signal to noise ratio.

5. The ultrasound processing system of claim 1, wherein the processing electronics normalize the selection value of the selected single comparison set for each section of the plurality of sections for the first frame of the plurality of frames.

6. The ultrasound processing system of claim 1, wherein the processing electronics select the selected single comparison set based on a desired displacement and/or strain.

7. The ultrasound processing system of claim 1, wherein the processing electronics select the selected single comparison set to use based on a weighted system, the weighted system based on a displacement and/or strain average and a desired displacement and/or strain.

8. The ultrasound processing system of claim 1, wherein the processing electronics predict a periodicity of motion.

9. The ultrasound processing system of claim 1, wherein the processing electronics generate a feedback including the selected single comparison set.

10. The ultrasound processing system of claim 9, wherein the processing electronics use the feedback of the selected single comparison set to estimate at least one of a displacement or a strain of at least one previous frame of the plurality of frames.

11. The ultrasound processing system of claim 1, wherein the plurality of frames are divided into the plurality of sections based on depth, wherein the plurality of sections includes a first section corresponding to a first depth and a second section corresponding to a second depth; the first comparison set has the corresponding selection value based on the first section of the first frame of the plurality of frames and the second section of the second frame of the plurality of frames; and the second comparison set has the corresponding selection value based on the first section of the first frame of the plurality of frames and the second section of the third frame of the plurality of frames.

12. The ultrasound processing system of claim 1, wherein the generating the plurality of comparison sets and corresponding selection values comprises performing comparisons for all comparison sets and all sections in a designated segment of data; and after the performing comparisons for all comparison sets and all sections in the designated segment of data, the selecting the single comparison set from the plurality of comparison sets is performed based on previous frame selections.

13. A method of signal to noise ratio improvement in elastography using time-varying frame selection strain estimation, the method comprising:
receiving imaging and displacement and/or strain data including a plurality of frames including at least a first frame, a second frame previous to the first frame, and a third frame previous to the first frame;
dividing each frame of the plurality of frames into a plurality of sections, wherein each frame of the plurality of frames is divided into the plurality of sections based on a strain decay at a given depth;
for each particular section of the plurality of sections for the first frame of the plurality of frames:
generating a plurality of comparison sets and corresponding selection values using the imaging and displacement and/or strain data including at least a first comparison set having a corresponding selection value based on the particular section of the first frame of the plurality of frames and the particular section of the second frame of the plurality of frames and a second comparison set having a corresponding selection value based on particular section of the first frame of the plurality of frames and the particular section of the third frame of the plurality of frames, each selection value including at least one of a displacement or a strain;
selecting, responsive to generating the plurality of comparison sets, a frame comparison set from the plurality of comparison sets based on the corresponding selection values of each of the plurality of comparison sets; and
assigning the selection value of the selected frame comparison set to particular section of the first frame;
generating an image based on the plurality of frames using the selected frame comparison set and the assigned the selection value for each section of the plurality of sections of the first frame, and
displaying the image.

14. The method of claim 13, wherein after a defined period, the selected frame comparison set is used to estimate a final displacement and/or strain through a feedback.

15. The method of claim 14, wherein the estimated final strain is estimated by normalizing the assigned selection value for each section of the plurality of sections of the first frame.

16. The method of claim 13, wherein the selected frame comparison set is selected based on at least one of a mean or a signal to noise ratio (SNR) of the assigned selection value for each section of the plurality of sections of the first frame.

17. The method of claim 13, wherein the plurality of frames are divided into the plurality of sections based on depth, wherein the plurality of sections includes a first section corresponding to a first depth and a second section corresponding to a second depth; the first comparison set has the corresponding selection value based on the first section of the first frame of the plurality of frames and the second section of the second frame of the plurality of frames; and the second comparison set has the corresponding selection value based on the first section of the first frame of the plurality of frames and the second section of the third frame of the plurality of frames.

18. The method of claim 13, wherein the generating the plurality of comparison sets and corresponding selection values comprises performing comparisons for all comparison sets and all sections in a designated segment of data; and after the performing comparisons for all comparison sets and all sections in the designated segment of data, the selecting the frame comparison set from the plurality of comparison sets is performed based on previous frame selections.

19. An ultrasound machine comprising
one or more processors and a memory storing computer-readable instructions that when executed by the one or more processors, cause the one or more processors to:
receive ultrasound returns representative of an ultrasound scene for display including a plurality of frames;
divide each of the plurality of frames into sections based on a strain decay at a given depth;
generate, for each section in a first frame of the plurality of frames, a plurality of comparison sets wherein for each comparison set, the section of the first frame is compared to the corresponding section of a different frame of the plurality of frames;
generate, for each comparison set of each section in the first frame of the plurality of frames, a selection value based on the compared sections of the comparison set;
select, responsive to generating the selection values, a single comparison set from the plurality of comparison sets for each section of the first frame based on the generated selection values of the comparison sets;
generate an elastic image based on the selected single comparison set for each section of the first frame.

20. The ultrasound machine of claim 19, wherein the plurality of frames are divided into sections based on depth including at least a first section corresponding to a first depth and a second section corresponding to a second depth; the first comparison set has the corresponding selection value based on the first section of the first frame of the plurality of frames and the second section of the second frame of the plurality of frames; and the second comparison set has the corresponding selection value based on the first section of the first frame of the plurality of frames and the second section of the third frame of the plurality of frames.

21. The ultrasound machine of claim 19, wherein the one or more processors comprise a frame comparator configured to generate the plurality of comparison sets by performing comparisons for all comparison sets and all sections in a designated segment of data; and after the frame comparator has passed the designated segment, the frame comparator become passive and the one or more processors is configured to select the single comparison set based on previous frame selections.

\* \* \* \* \*